United States Patent
Campbell et al.

(10) Patent No.: US 9,855,200 B2
(45) Date of Patent: *Jan. 2, 2018

(54) ORAL CARE FORMULATIONS THAT ENHANCE AMOUNT OF SOLUBLE ZINC

(75) Inventors: Thomas S. Campbell, Flemington, NJ (US); Thomas J. Boyd, Metuchen, NJ (US); Steven W. Fisher, Middlesex, NJ (US); Michael Prencipe, Princeton Junction, NJ (US)

(73) Assignee: Colgate-Palmolive Company, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 13/266,938

(22) PCT Filed: May 26, 2010

(86) PCT No.: PCT/US2010/036140
§ 371 (c)(1),
(2), (4) Date: Oct. 28, 2011

(87) PCT Pub. No.: WO2010/138544
PCT Pub. Date: Dec. 2, 2010

(65) Prior Publication Data
US 2012/0042893 A1    Feb. 23, 2012

Related U.S. Application Data

(60) Provisional application No. 61/181,116, filed on May 26, 2009.

(51) Int. Cl.
| | | |
|---|---|---|
| *A61K 8/27* | (2006.01) | |
| *A61K 8/34* | (2006.01) | |
| *A61K 8/73* | (2006.01) | |
| *A61K 8/81* | (2006.01) | |
| *A61K 8/86* | (2006.01) | |

(52) U.S. Cl.
CPC ............. *A61K 8/27* (2013.01); *A61K 8/345* (2013.01); *A61K 8/73* (2013.01); *A61K 8/731* (2013.01); *A61K 8/8164* (2013.01); *A61K 8/86* (2013.01); *A61K 2800/56* (2013.01); *A61K 2800/592* (2013.01)

(58) Field of Classification Search
None
See application file for complete search history.

(56) References Cited

U.S. PATENT DOCUMENTS

| | | | |
|---|---|---|---|
| 4,022,880 A | 5/1977 | Vinson et al. | |
| 4,138,477 A | 2/1979 | Gaffar | |
| 4,820,506 A | 4/1989 | Kleinberg et al. | |
| 4,839,157 A | 6/1989 | Mei-King Ng et al. | |
| 4,894,220 A | 1/1990 | Nabi et al. | |
| 4,900,552 A | 2/1990 | Sanvordeker et al. | |
| 5,047,244 A | 9/1991 | Sanvordeker et al. | |
| 5,188,821 A * | 2/1993 | Gaffar | A61K 8/24 106/35 |
| 5,202,112 A * | 4/1993 | Prencipe et al. | 424/52 |
| 5,385,727 A * | 1/1995 | Winston | A61K 8/19 424/49 |
| 5,695,746 A | 12/1997 | Garlick, Jr. et al. | |
| 5,700,478 A | 12/1997 | Biegajski et al. | |
| 5,948,430 A | 9/1999 | Zerbe et al. | |
| 6,123,965 A | 9/2000 | Jacob et al. | |
| 6,241,974 B1 | 6/2001 | White, Jr. et al. | |
| 6,287,541 B1 | 9/2001 | Creeth et al. | |
| 6,315,986 B1 | 11/2001 | Wong et al. | |
| 6,596,298 B2 | 7/2003 | Leung et al. | |
| 6,669,929 B1 | 12/2003 | Boyd et al. | |
| 2003/0053962 A1 | 3/2003 | Zerbe et al. | |
| 2003/0054034 A1 | 3/2003 | Leung et al. | |
| 2004/0126332 A1 | 7/2004 | Boyd et al. | |
| 2004/0247647 A1 | 12/2004 | Ivory et al. | |
| 2005/0019273 A1 | 1/2005 | Boyd et al. | |
| 2005/0276760 A1* | 12/2005 | Lokken | 424/53 |
| 2007/0020201 A1* | 1/2007 | Boyd et al. | 424/52 |

(Continued)

FOREIGN PATENT DOCUMENTS

| | | | |
|---|---|---|---|
| JP | H09-175968 | 7/1997 | |
| NL | EP 0295116 A1 * | 12/1988 | A61K 8/24 |

(Continued)

OTHER PUBLICATIONS

EWG "tetrasodium pyrophosphate," accessed 2017; https://www.ewg.org/skindeep/ingredient/706515/TETRASODIUM_PYROPHOSPHATE/.*
Dow "METHOCEL Cellulose Ethers in Aqueous Systems for Tablet Coating," Jul. 2002.*
Gan et al., 2009. "Antibacterial Activity of Zinc-Chelator Complexes," The Preliminary Program for IADR/AADR/CADR 87th General Session and Exhibition (Apr. 1-4, 2009).
International Search Report and Written Opinion in International Application No. PCT/US10/036041, dated Mar. 28, 2011.

(Continued)

*Primary Examiner* — David J Blanchard
*Assistant Examiner* — Alissa Prosser

(57) ABSTRACT

An oral care composition and method are described in which the composition includes a film or a plurality of film fragments entrained in a carrier. The film or plurality of film fragments comprises a zinc compound and the carrier comprises a polysaccharide and a maleic anhydride copolymer. The composition and methods provide benefits including one or more of increased consumer acceptability, improved solubility of zinc thus permitting the use of lower amounts of zinc compounds and reducing the adverse astringency associated with zinc, decreased adverse reactions brought about by the presence of zinc ions, enhanced aesthetics, improved stability for active or other functional materials, and controlled delivery of active materials such as zinc.

10 Claims, No Drawings

(56) References Cited

U.S. PATENT DOCUMENTS

| | | | |
|---|---|---|---|
| 2007/0148213 A1* | 6/2007 | Ibrahim | A61K 8/0208 424/443 |
| 2007/0183989 A1 | 8/2007 | Prencipe et al. | |
| 2008/0014224 A1 | 1/2008 | Boyd et al. | |
| 2008/0138369 A1 | 6/2008 | Boyd et al. | |
| 2008/0181856 A1* | 7/2008 | Prencipe | A61K 8/24 424/57 |

FOREIGN PATENT DOCUMENTS

| | | | |
|---|---|---|---|
| WO | WO 01/34108 | 5/2001 | |
| WO | WO 03/015749 | 2/2003 | |
| WO | WO 2004/060335 | 7/2004 | |
| WO | WO 2005039499 A2 * | 5/2005 | A61K 9/006 |
| WO | WO 2007/013937 | 2/2007 | |
| WO | WO 2007/076444 | 7/2007 | |
| WO | WO 2007/076466 | 7/2007 | |
| WO | WO 2008/014379 | 1/2008 | |
| WO | WO 2008/041055 | 4/2008 | |
| WO | WO 2008/130764 | 10/2008 | |
| WO | WO 2010/114546 | 10/2010 | |

OTHER PUBLICATIONS

International Search Report and Written Opinion in International Application No. PCT/US10/036140, dated Mar. 25, 2011.

International Search Report and Written Opinion in International Application No. PCT/US10/036143, dated Mar. 25, 2011.

Muller et al., 1996, "The Effect of pH on the Corrosion Inhibition of Zinc Pigments by Phenol Derivatives," Corrosion Science 38(11):1869-1875.

Vasir et al., 2003, "Bioadhesive microspheres as a controlled drug delivery system," Int. J. Pharmaceutics 255(1-2):13-32.

Hider et al., 1990, "Facilitated uptake of zinc into human erythrocytes. Relevance to the treatment of sickle-cell anaemia," Biochem. Pharmacol. 39(6):1005-1012 (resubmitting article in full).

Majithiya et al., 2008, "Mucoadhesion Enhancement: Enhancement of Mucoadhesion by Blending Anionic, Cationic & Nonionic Polymers," Drug Delivery Tech. 8:40-45 (resubmitting legible).

* cited by examiner

ORAL CARE FORMULATIONS THAT ENHANCE AMOUNT OF SOLUBLE ZINC

CROSS REFERENCE TO RELATED APPLICATIONS

This application is a national stage entry under 35 U.S.C. §371 of International Patent Application No. PCT/US2010/036140, filed 26 May 2010, which claims priority to U.S. Provisional Patent Application Ser. No. 61/181,116, filed on 26 May 2009, the entireties of which are incorporated herein by reference.

BACKGROUND

This application relates to oral and personal care compositions, and more particularly to compositions comprising a film entrained in a carrier, in which the film includes an active agent. Such compositions include, for example, dentifrices.

The aesthetic appeal of such compositions is important, and can have significant effects on consumer acceptance and usage. Aesthetic effects have been acknowledged to play an important role in consumer acceptance of many products. Although such products have met with consumer approval, the art seeks to further improve the aesthetic effects as well as the cosmetic and therapeutic benefits of these products. Indeed, many such compositions known in the art are deficient in one or more attributes.

Compositions for enhancing health, hygiene or appearance, such as oral care compositions, skin care compositions and hair care compositions, are used by millions of people. These compositions are used for a wide variety of purposes, including for enhancing personal health, hygiene, and appearance, as well as for preventing or treating a variety of diseases and other conditions in humans and in animals.

The formulation of such compositions presents a number of challenges. They must be pharmaceutically and/or cosmetically acceptable for their intended use. Compositions that contain therapeutic active materials preferably deliver the active at effective levels, avoiding undue chemical degradation. Similarly, compositions containing cosmetically functional materials must deliver the material to, e.g., the oral cavity, skin or hair at effective levels under the conditions that they are typically used by the consumer.

Water-soluble films for oral administration of therapeutic agents are well known in the art. It is also known in the art to use such films for administering a breath freshening agent, e.g., menthol. The known films for administering breath freshening agents and/or active pharmaceutical agents are generally comprised of at least one water-soluble polymer suitable for human consumption and at least one compound that enhances the wettability of the water-soluble polymer, typically selected from polyalcohols, surfactants and plasticizers. For example, U.S. Pat. No. 5,948,430, disclosure of which is incorporated by reference herein in its entirety, describes a monolayer film that can be adhered to the oral cavity to release a pharmaceutically or cosmetically active ingredient, wherein the film comprises at least one water-soluble polymer; at least one member selected from the group consisting of a polyalcohol, a surfactant and a plasticizer; at least one cosmetic or pharmaceutically active ingredient; and a flavoring agent.

U.S. Pat. No. 5,700,478, the disclosure of which is incorporated by reference herein in its entirety, describes a laminated device for controlled release of a substance within a mucosa-lined body cavity including a water-soluble adhesive layer comprised of a water-soluble polymer and a water-soluble plasticizer, and a water-soluble polymer layer. This patent teaches a multiple layer laminate that dissolves relatively slowly for controlled or sustained release of a substance.

U.S. Pat. No. 4,900,552, the disclosure of which is incorporated by reference herein in its entirety, describes a trilaminate film suitable for prolonged and sustained delivery of an active ingredient in a buccal cavity. The trilaminate includes a hydratable muco-adhesive base layer; a non-adhesive reservoir layer; and a water-impermeable barrier sandwiched between and bonded to the base layer and the reservoir layer. This patent discloses slowly disintegrating films for prolonged or sustained release of a substance.

U.S. Pat. No. 5,047,244, the disclosure of which is incorporated by reference herein in its entirety, discloses a therapeutic dosage form comprising an anhydrous but hydratable monolithic polymer matrix that contains amorphous fumed silica as well as a therapeutic agent, and a water-insoluble barrier layer secured to the polymer matrix and defining a non-adhesive face. This patent does not disclose rapidly disintegrating films, but instead contemplates compositions that are capable of providing improved availability of therapeutic agents from a controlled release muco-adhesive carrier system.

U.S. Pat. No. 6,669,929, and U.S. Patent Application Publication No. 2003/0053962, the disclosures of each of which are incorporated by reference herein in their entirety, disclose film forming agents useful in oral care compositions. The films dissolve in the mouth and release functional components, typically flavorants.

It is known to incorporate flavorants, colorants, and some active components in films that dissolve in the oral cavity. These films are used either by themselves as breath freshening strips, teeth whitening strips, or as polymer flakes dispersed throughout an oral care composition. It also is known to incorporate zinc salts in dentifrice formulations. Use of various zinc salts often is limited by the solubility of the zinc, undesirable consumer astringency when higher levels of zinc are utilized, and the reactivity of the zinc once zinc ions are available for reaction (i.e., the zinc ions sometimes cause adverse reactions within the formulation).

Thus, there is an ongoing need for new oral and personal care compositions, and methods of their use.

SUMMARY

The present invention provides, in various embodiments, oral and personal care compositions comprising a film entrained in a carrier, in which the film includes an active agent. In one embodiment, the film is provided as a plurality of film fragments. In various embodiments, the present invention provides compositions comprising a plurality of lamellar fragments in a carrier.

In one embodiment, the oral care composition comprises a film entrained in a carrier, a zinc-containing compound contained in the film, a polysaccharide, and a maleic anhydride copolymer. In a preferred embodiment, the oral care composition is in the form of a dentifrice.

The embodiments also provide methods for administering a zinc compound to a human or animal subject in need thereof, the method including topically applying to the subject an oral care composition comprising a film entrained in a carrier, a zinc-containing compound contained in the film, a polysaccharide, and a maleic anhydride copolymer. In various methods, such methods further comprise disrupting the film after the topical application.

Compositions and methods of this invention afford benefits over compositions and methods among those known in the art. Such benefits include one or more of increased consumer acceptability, improved solubility of zinc thus permitting the use of lower amounts of zinc compounds and reducing the adverse astringency associated with zinc, decreased adverse reactions brought about by the presence of zinc ions, enhanced aesthetics, improved stability for active or other functional materials, and controlled delivery of active materials such as zinc. Further benefits and embodiments of the present invention are apparent from the description set forth herein.

DESCRIPTION

The present invention provides compositions and methods, for administration to, or use with, a human or other animal subject. Preferably, specific materials and compositions to be used in this invention are, accordingly, pharmaceutically- or cosmetically-acceptable. As used herein, such a "pharmaceutically acceptable" or "cosmetically acceptable" component is one that is suitable for use with humans and/or animals to provide the desired therapeutic, sensory, decorative, or cosmetic benefit without undue adverse side effects (such as toxicity, astringent taste, irritation, and allergic response) commensurate with a reasonable benefit/risk ratio. The following definitions and non-limiting guidelines must be considered in reading and interpreting the description of this invention set forth herein.

The headings (such as "Introduction" and "Summary,") used herein are intended only for general organization of topics within the disclosure of the invention, and are not intended to limit the disclosure of the invention or any aspect thereof. In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof.

The citation of references herein does not constitute an admission that those references are prior art or have any relevance to the patentability of the invention disclosed herein. All references cited in the Description section of this specification are hereby incorporated by reference in their entirety.

The description and specific examples, while indicating embodiments of the invention, are intended for purposes of illustration only and are not intended to limit the scope of the invention. Recitation of multiple embodiments having stated features is not intended to exclude other embodiments having additional features, or other embodiments incorporating different combinations of the stated features. Specific Examples are provided for illustrative purposes of how to make, use and practice the compositions and methods of this invention and, unless explicitly stated to recite activities that have been done (i.e., using the past tense), are not intended to be a representation that given embodiments of this invention have, or have not, been performed.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. As used herein, the word "include," and its variants, is intended to be non-limiting, such that recitation of items in a list is not to the exclusion of other like items that may also be useful in the materials, compositions, devices, and methods of this invention. In a similar manner, the description of certain advantages or disadvantages of known materials and methods is not intended to limit the scope of the embodiments to their exclusion. Indeed, certain embodiments may include one or more known materials or methods, without suffering from the disadvantages discussed herein.

As used herein, the term "comprising" means that other steps and other components that do not affect the end result may be utilized. The term "comprising" encompasses the expressions "consisting of," and "consisting essentially of." The expression "effective amount," as used herein denotes an amount of a compound or composition sufficient to significantly induce a positive benefit, preferably an oral health benefit, but low enough to avoid serious side effects, i.e., to provide a reasonable benefit to risk ratio, within the sound judgment of a person having ordinary skill in the art. The use of singular identifiers such as "the," "a," or "an" is not intended to be limiting solely to the use of a single component, but may include multiple components.

The oral care compositions of the various embodiments preferably are in the form of a dentifrice. The term "dentifrice" as used throughout this description, denotes a paste, gel, or liquid formulation. The dentifrice may be in any desired form, such as deep striped, surface striped, multilayered, having a gel surround the paste, or any combinations thereof. The film contained in the oral care composition may be of any desired shape or structure, including multiple small strips, or one continuous strip.

The expressions "carrier" or "aqueous carrier" as used throughout this description denote any safe and effective materials for use herein. Such materials include, for example, thickening agents, humectants, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof.

All percentages and ratios used herein are by weight of the oral care composition, unless otherwise specified. All measurements are made at 25° C., unless otherwise specified.

The present invention provides oral or personal care compositions comprising a film entrained in a carrier, wherein the film comprises a zinc compound. As referred to herein, an "oral or personal care composition" is any composition that is suitable for administration or application to a human or animal subject for enhancing the health, hygiene or appearance of the subject, including the prevention or treatment of any physiologic condition or disorder, and providing sensory, decorative or cosmetic benefits and combinations thereof. Compositions among those provided herein include oral care compositions, skin care compositions, hair care composition, topical pharmaceutical compositions, and ocular compositions. By "oral care composition" as used herein is meant a composition for which the intended use can include oral care, oral hygiene, or oral appearance, or for which the intended method of use can comprise administration to the oral cavity. By "skin care composition" as used herein is meant a composition for which the intended use can include promotion or improvement of health, cleanliness, odor, appearance, or attractiveness of skin.

Embodiments of this invention comprise a film. As referred to herein, a "film" is a material having a substantially lamellar structure. A "lamellar" structure has, or is capable of having, a size in one or two dimensions (e.g., the x- or y-dimensions) that is substantially greater than the thickness of the structure in a third dimension (e.g., the z-direction). Lamellar structures among those useful herein include those that are substantially planar, layered, or lamelliform. In one embodiment, the lamellar structure is substantially planar, having a size in both the x- and y-dimensions that is substantially greater than the z-direction. In other embodiments, the lamellar structure is non-planar. In one embodiment, a film of this intention comprises a substantially continuous surface that can appear as a substantially flat surface, although in some embodiments the film is deformed. In such embodiments, the film can have any of a number of shapes, including having a smooth curved surface.

Films among those useful herein may be rigid or plastic, comprising any of a variety of materials, including materials selected from the group consisting of film forming materials, clays, waxes, and mixtures thereof. In one embodiment, the film comprises a film forming polymer. Film forming polymers among those useful herein include materials selected from the group consisting of water soluble polymers, water dispersible polymers, water insoluble polymers, and mixtures thereof.

In some embodiments, a film comprises at least one film forming material. In certain embodiments, a film forming material is a polymer. Polymers useful herein include hydrophilic polymers and hydrophobic polymers. In certain embodiments, the polymer is a water soluble polymer. In some embodiments, the polymer is a water soluble, breakable polymer that dissolves during use, such as, for example, during toothbrushing. The dissolution can occur as a result of, for example, shearing and/or exposure to a solvent comprising a high concentration of water, such as saliva. In some embodiments, the polymer is insoluble but breakable in water by being dispersible, i.e., the polymer breaks down into small fragments, for example, as a result of shearing. In some embodiments, a polymer is insoluble but swellable. In configurations in which a polymer does not break down during use, the polymer can be a water-repellant polymer or an aqueous-stable hydrophilic polymer such as certain types of cellulose, for example paper. In some embodiments, a film fragment can comprise a mixture of film forming materials.

Water soluble polymers among those useful herein include cellulose ethers, methacrylates, polyvinylpyrrollidone, and mixtures thereof. In one embodiment, the polymer is a cellulose ether, including those selected from the group consisting of hydroxyalkyl cellulose polymers such as hydroxypropyl methyl cellulose (HPMC), hydroxypropyl cellulose, hyrdoxyethyl cellulose, methyl cellulose, carboxymethyl cellulose, and mixtures thereof. Other polymers among those useful herein include polyvinylpyrrolidone, cross-linked polyvinyl pyrrolidone, polyvinylpyrrolidone-vinyl acetate copolymer, polyvinylalcohol, polyacrylic acid, poly acrylate polymer, cross-linked polyacrylate polymer, cross-linked polyacrylic acid (e.g, Carbopol®), polyethylene oxide, polyethylene glycol, poly vinyl alkyl ether-maleic acid copolymer (such as Gantrez®) and carboxy vinyl polymer; natural gums such as sodium alginate, carrageenan, xantham gum, gum acacia, arabic gum, guar gum, pullulan, agar, chitin, chitosan, pectin, karaya gum, zein, hordein, gliadin, locust bean gum, tragacantha and other polysaccharides; starches such as maltodextrin, amylose, high amylose starch, corn starch, potato starch, rice starch, tapioca starch, pea starch, sweet potato starch, barley starch, wheat starch, waxy corn starch, modified starch (e.g. hydroxypropylated high amylose starch), dextrin, levan, elsinan and gluten; and proteins such as collagen, whey protein isolate, casein, milk protein, soy protein and gelatin.

Non-limiting examples of water dispersable and swellable polymers include modified starch, alginate esters, divalent or multivalent ion salts of alginates. Non-limiting examples of water insoluble polymers include polymers soluble in at least one organic solvent, such as cellulose acetate, cellulose nitrate, ethylene-vinyl acetate copolymers, vinyl acetate homopolymer, ethyl cellulose, butyl cellulose, isopropyl cellulose, shellac, silicone polymer (e.g. dimethylsilicone), PMMA (poly methyl methacrylate), cellulose acetate phthalate and natural or synthetic rubber; polymers insoluble in organic solvents, such as cellulose, polyethylene, polypropylene, polyesters, polyurethane and nylon.

The films useful in the various embodiments can be made in accordance with the methods described in U.S. Pat. No. 6,669,929, and U.S. Patent Application Publication No. 2003/0053962, the disclosures of which are incorporated by reference herein in their entirety. The zinc compounds contained within the film can be incorporated into the film during film manufacture using techniques known in the art. A person having ordinary skill in the art will be capable of making the film containing the zinc compound, using the guidelines provided herein.

In various embodiments, the oral care compositions comprise a plurality of lamellar film fragments entrained in a carrier. In one embodiment, the composition comprises a film, wherein the film comprises lamellar fragments of the film material. In one embodiment, the composition comprises a carrier having distributed therein a plurality of lamellar fragments, wherein the fragments comprise a matrix and a functional zinc compound material. In one such embodiment, the matrix comprises a film. Such fragments may be of any of a variety of shapes or forms, including semi-solid or solid discrete portions, fragments, particles, flakes, or combinations thereof. In various embodiments, the film comprises a first plurality of fragments and a second plurality of fragments, wherein the first plurality of fragments differ in composition or appearance from the second plurality of fragments. Such difference in composition or appearance can be in any aspect of the composition of the fragment (e.g., different film components, different functional material, different formulation colorant), different appearance (e.g., shape, color, texture, refractive index, reflective index), or combinations thereof.

In various embodiments, the fragments exhibit perceivable contrast with the carrier. The perceivable contrast can be sensory contrast, such as optical contrast, tactile contrast, taste contrast, or olfactory contrast. In some configurations, optical contrast can be color contrast, or a difference in refractive index or reflective index. In some configurations, color contrast can be imparted by one or more colorants that comprise different components of the composition. In various embodiments, the present invention provides compositions comprising a plurality of film fragments in a carrier, wherein said fragments are visibly discernable. As referred to herein, "visibly discernable" refers to one or more characteristics of a fragment which cause the fragment to have a different physical appearance, preferably to the naked eye, relative to the carrier in which the fragment is entrained. Such characteristics include color, opacity, refractive index, reflective index, size, shape, and combinations thereof.

In various embodiments, the fragments have a non-random shape. In one embodiment, a "non-random" shape is a shape which results from a manufacturing process of shaping, cutting, or other forming process by which a specific shape is imparted to a fragment. In such embodiments, a non-random shape is distinguished from such shapes that result from simple precipitation or grinding of a material. In one embodiment, a "non-random" shape is "repeating," wherein the composition comprises a plurality of fragments have substantially the same shape. Such repeating shape may have any of a variety of forms, and may be selected based on a variety of aesthetic or functional criteria. In certain embodiments, the shape of a film fragment can be a recognizable shape. In certain embodiments, a film fragment can comprise a nonrandom shape. Such shapes include simple geometric shapes, such as polygons and elliptical shapes, such as triangles, quadrilaterals (such as a square, a rectangle, a rhombus), pentagons, hexagons, oval, and circles. In one embodiment, the repeating shape is a square. Repeating shapes include, in other embodiments, shapes that are representative of figures or animate or inanimate objects, such as stars, hearts, gems, flowers, trees, shamrocks, a letter of an alphabet, numbers, animals, people, and faces. In various embodiments, the composition comprises a single repeating shape. In other embodiments, the composition comprises a plurality of fragments having a plurality of repeating shapes. In one embodiment, the compositions of the present invention comprise a plurality of first film fragments having a first repeated shape and a plurality of second film fragments having a second repeated shape, wherein the first repeated shape is different from the second repeated shape.

In various embodiments, the size of the fragments is not critical, and may be determined pursuant to any of a variety of criteria, including manufacturing convenience, affect on visual appearance, surface area, affect on texture in the composition, and combinations thereof. In some embodiments, the film fragments can be up to about 1 inch (25.4 mm) in length in the longest dimension. As referred to herein, "long dimension" is the dimension of a fragment in length or width (i.e., in the x- and y-dimensions, as the fragment is, or is deformed to be in a planar shape) in a dimension substantially perpendicular to the "thickness" or shortest dimension of the fragment (i.e., the z-dimension). It is understood that in various embodiments comprising a plurality of fragments, the fragments may be present in a range of sizes due to a variety of factors, including random variation in size, manufacturing tolerances, and intentional sizing or mixing of the fragments through sieving or similar means. As referred to herein, sizes refer to the average size of fragments in a given plurality of fragments.

In various embodiments, the fragments are from about 0.2 mm to about 15 mm in long dimension. In various embodiments, the long dimension of the fragments is from 0.2 mm to about 10 mm, from about 0.5 mm to about 10 mm, from about 0.8 mm to about 8 mm, from about 0.9 mm to about 5 mm, from about 1.0 mm to about 5 mm, or from about 1.5 mm to about 2.5 mm. In some embodiments, the long dimension of the fragments is at least about 3 mm, and can be from about 6 mm to about 13 mm. In certain embodiments, a plurality of film fragments is greater than about 600 microns in the longest dimension. In certain embodiments, a plurality of film fragments is greater than about 1 millimeter in the longest dimension.

In various embodiments, the fragments of the present invention have a thickness of from about 1 mil (thousandth of an inch, 25.4 microns) to about 3 mils (76.2 microns). In various embodiments, the fragments have a thickness of less than about 4 mils or less about 100 microns and from about 0.1 mils (2.54 microns) up to about 10 mils (254 microns), from about 0.5 mils (12.7 microns) up to about 5 mils (127 microns), from about 1.4 mils (35.6 microns) to about 2.0 mils (50.8 microns).

In some embodiments, the compositions of the present invention comprise fragments having an aspect ratio of at least about 5:1. As referred to herein, "aspect ratio" of a fragment is the ratio of the diameter of the smallest imaginary sphere that can enclose the object to the diameter of the largest imaginary sphere that can be completely inside the object and tangent to the surfaces of the object. For example, the aspect ratio of a sphere is 1:1; in another example, the aspect ratio of a cylinder that is 2 inches (50.8 mm) long and ¼ inch (6.35 mm) in diameter is slightly over 8:1; in yet another example, a film fragment of the present invention that is 1 mil (25.4 microns) in thickness, 1 inch (25.4 mm) in length, and 1 inch (25.4 mm) wide has an aspect ratio of about 1414:1.

In some embodiments, the compositions of the present invention comprise fragments having an aspect ratio of at least about 10:1. In various embodiments, the fragments have an aspect ratio of from about 5:1 to about 10,000:1, from about 5:1 to about 500:1, from about 10:1 to about 1,000:1, from about 10:1 to about 100:1, from about 20:1 to about 100:1, or from about 25:1 to about 35:1.

In various embodiments, the film comprises a formulation colorant that imparts a color to the film, the composition, or both. In various embodiments, the film fragments contrast with the carrier, and are white, black, or of any color that is visible against or contrasts with the carrier background. Formulation colorants among those useful herein include non-toxic water soluble dyes or pigment, such as, for example, metallic oxide "lakes." In certain embodiments, the colorant is approved for incorporation into a food or drug by a regulatory agency, such as FD&C or D&C pigments and dyes approved by the FDA for use in the United States. Colorants among those useful herein include FD&C Red No. 3 (sodium salt of tetraiodofluorescein), Food Red 17, disodium salt of 6-hydroxy-5-{(2-methoxy-5-methyl-4-sulphophenyl)azo}-2-naphthalenesulfonic acid, Food Yellow 13, sodium salt of a mixture of the mono and disulphonic acids of quinophtalone or 2-(2-quinolyl) indanedione, FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphtol-6-monosulfonate), FD&C Green No. 3 (disodium salt of 4-{[4-(N-ethyl-p-sulfobenzylamino)-phenyl]-(4-hydroxy-2-sulfoniumphenyl)-methylene}-[1-(N-ethyl-N-p-sulfobenzyl)-A-3,5-cyclohexadienimine], FD&C Blue No. 1 (disodium salt of dibenzyldiethyl-diaminotriphenylcarbinol trisulfonic acid anhydrite), FD&C Blue No. 2 (sodium salt of disulfonic acid of indigotin), and mixtures thereof in various proportions. In one embodiment, the colorant comprises a water insoluble inorganic pigment, such as titanium dioxide, chromium oxide green, phthalocyanine green, ultramarine blue, ferric oxide, or a water insoluble dye lake. In some embodiments, dye lakes include calcium or aluminum salts of an FD&C dye such as FD&C Green #1 lake, FD&C Blue #2 lake, D&C Red #30 lake or FD&C # Yellow 15 lake. In certain embodiments, a water soluble dye, such as, for example, FD&C Blue #1, is contained within a water-insoluble polymer such as, for example polyethylene such as that found in polyethylene beads (e.g., Microblue Spectrabeads, sold by Micropowders, Inc.). In certain embodiments, the film comprises a dye such as D&C Red #30. In certain embodiments, a white colorant is used, for example titanium dioxide ($TiO_2$), titanium dioxide coated mica (e.g., Timiron), a mineral, or a clay. In certain embodiments, the colorant is a non-bleeding dye. In various embodiments, the film comprises a colorant at a level of from about from 0.5% to about 20% by weight of the film, or from about 1% to about 15% by weight of the film, or from about 3% to about 12% by weight of the film. In one embodiment, the compositions of the present invention comprise a first plurality of film fragments comprising a first color, and a second plurality of film fragments comprising a second color. Preferably, the second color is different than the first color.

The film of the present invention, in various embodiments, disintegrates during use of the composition. In other embodiments, the film does not disintegrate during use of the composition. In some embodiments, the film releases a material, such as the zinc compound, into the carrier. As referred to herein, "disintegrate" refers to physical disruption of the film or fragment material, so as to produce a film or film fragments of reduced size compared to the original film. Such disruption may be through mechanical, chemical, or physical-chemical means. The disintegration can result, for example, from shearing, grinding, or exposure to elevated temperatures during use. In various dentifrice embodiments of the present invention, such disintegration results from brushing of the composition on the teeth of the subject using the composition. In one embodiment, the film disintegrates so as to release a functional material (as further described herein). In some embodiments, a film fragment can disintegrate into small pieces that are not visually discernable. In some embodiments, the film fragments disintegrate to collectively form a colloid or gel.

In various embodiments, the film may comprise, in addition to the zinc compound other therapeutic actives. As referred to herein, a therapeutic active is a material that is useful for the prevention or treatment of a physiological disorder or condition. Such disorders or conditions include those of the oral cavity (including the teeth and gingiva), skin, hair, and eyes. The specific therapeutic active is preferably determined according to the desired utility of the composition. Such actives include the following.

A. antimicrobial agents, such as triclosan, cetyl pyridium chloride, domiphen bromide, quaternary ammonium salts, sanguinarine, fluorides, alexidine, octonidine, EDTA, essential oils such as thymol, methyl salicylate, eucalyptol and menthol, and the like, B. non-steroidal anti-inflammatory drugs, such as aspirin, acetaminophen, ibuprofen, ketoprofen, diflunisal, fenoprofen calcium, naproxen, tolmetin sodium, indomethacin, and the like, C. anti-tussives, such as benzonatate, caramiphen edisylate, menthol, dextromethorphan hydrobromide, chlophedianol hydrochloride, and the like, D. decongestants, such as pseudoephedrine hydrochloride, phenylepherine, phenylpropanolamine, pseudoephedrine sulfate, and the like, E. anti-histamines, such as brompheniramine maleate, chlorpheniramine maleate, carbinoxamine maleate, clemastine fumarate, dexchlorpheniramine maleate, diphenhydramine hydrochloride, diphenylpyraline hydrochloride, azatadine meleate, diphenhydramine citrate, doxylamine succinate, promethazine hydrochloride, pyrilamine maleate, tripelennamine citrate, triprolidine hydrochloride, acrivastine, loratadine, brompheniramine, dexbrompheniramine, and the like, F. expectorants, such as guaifenesin, ipecac, potassium iodide, terpin hydrate, and the like, G. anti-diarrheals, such a loperamide, and the like, H. $H_2$-antagonists, such as famotidine, ranitidine, and the like; and I. proton pump inhibitors, such as omeprazole, lansoprazole, and the like, J. general nonselective CNS depressants, such as aliphatic alcohols, barbiturates and the like, K. general nonselective CNS stimulants such as caffeine, nicotine, strychnine, picrotoxin, pentylenetetrazol and the like, L. drugs that selectively modify CNS function such as phenyhydantoin, phenobarbital, primidone, carbamazepine, ethosuximide, methsuximide, phensuximide, trimethadione, diazepam, benzodiazepines, phenacemide, pheneturide, acetazolamide, sulthiame, bromide, and the like, M. antiparkinsonism drugs such as levodopa, amantadine and the like, N. narcotic-analgesics such as morphine, heroin, hydromorphone, metopon, oxymorphone, levorphanol, codeine, hydrocodone, xycodone, nalorphine, naloxone, naltrexone and the like, O. analgesic-antipyretics such as salycilates, phenylbutazone, indomethacin, phenacetin and the like, P. psychopharmacological drugs such as chlorpromazine, methotrimeprazine, haloperidol, clozapine, reserpine, imipramine, tranylcypromine, phenelzine, lithium and the like.

The amount of medicament that can be used in the films can be dependent upon the dose needed to provide an effective amount of the medicament. In a particularly preferred embodiment, triclosan is not used, and the primary antibacterial agent is the zinc compound.

In various embodiments, therapeutic agents useful herein include anticaries agents, tartar control agents, antiplaque agents, periodontal actives, breath freshening agents, malodour control agents, whitening agents, antibacterials, steroids, anti-inflammatory agents, vitamins, proteins, conditioning agents, moisturizers, antiperspirant actives, deodorant actives, anesthetics, and mixtures thereof.

In certain oral care embodiments, the film or the oral care composition may comprise an oral care active, which is useful for the prevention or treatment of an oral care disorder or condition. Oral care actives among those useful herein include abrasives, anticaries agents, tartar control agents, antiplaque agents, periodontal actives, breath freshening agents, malodour control agents, tooth desensitizers, salivary stimulants, whitening agents, and combinations thereof. Active materials among those useful herein are described in U.S. Pat. No. 6,596,298, Leung et al.

Tartar control agents among those useful herein include dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$; long chain polyphosphates such as sodium hexametaphosphate; and cyclic phosphates such as sodium trimetaphosphate. In some configurations, a polyphosphate is a beta.-phase calcium pyrophosphate, such as disclosed in U.S. Pat. No. 6,241,974, White, Jr. In some embodiments, the film comprises an anticalculus agent at a level of about 15 to 20% by weight of the film.

Odor reducing agents useful herein include sulfur precipitating agents. Such sulfur-precipitating agents include metal salts, such as a copper salt or a zinc salt. Such salts include copper gluconate, zinc citrate and zinc gluconate. These zinc salts can be used in combination or in addition to the zinc compounds included in the film. In various embodiments, the film comprises sulfur precipitating agents at a level of from about 0.01 to about 30% by weight of film, from about 2% to about 2.5% by weight of film, or about 10% to about 20% by weight of film.

In a certain embodiments, the film and/or oral composition may include a saliva stimulating agent (a "succulent"). Such agents include those disclosed in U.S. Pat. No. 4,820,506, Kleinberg et al. In some configurations, a saliva stimulating agent can include a food acid such as citric, lactic, malic, succinic, ascorbic, adipic, fumaric and tartaric acids. In various embodiments, the film comprises a saliva stimulating agent at a level of from about 0.01 to about 12% by weight of the film, from about 1% to about 10% by weight of the film, or from about 2.5% to about 6% by weight of the film. In some embodiments, a saliva stimulating agent can be used in the amelioration of dry mouth.

In certain oral care embodiments, the film comprises other active materials, such as antibacterial agents such as magnolia extract, triclosan, grapeseed extract, thymol, methyl salicylate, eucalyptol, menthol, hop acids, cetyl pyridinium chloride, (including CPC/Zn and CPC+enzymes) and usnic acid; anti-inflammatory agents such a breath freshening agents (for example zinc gluconate, zinc citrate, zinc chlorite and alpha ionone); tooth desensitizers such as potassium nitrate, desensitizing polymers, and desensitizing minerals; anti-inflammatory agents such as magnolia extract, ursolic acid; aloe, and cranberry extract; vitamins such as pantheon, retinyl palmitate, folic acid, tocopherol acetate and Vitamin A; herbs or herbal extracts such as rosemary, oregano, chamomilla recutita, mentha piperita, salvia officinalis, orcommiphora and myrrha; proteins, such as milk proteins and enzymes such as peroxide-producing enzymes, amylase, plaque-disrupting agents such as papain, glucoamylase, glucose oxidase, and "next generation" enzymes; whitening agents such as hydrogen peroxide, urea peroxide and phosphate salts; medicinals, such as aspirin (acetyl salicylic acid), caffeine, and benzocaine; probiotics; abrasives such as silicas (including high cleaning silica); anti-caries agents such as stannous salts (e.g., stannous fluoride) or amino fluoride; a nitric oxide synthase inhibitor such as guanidinoethyldisulfide; calcium; antiattachment ingredients, such as polyumylphosphonic acid; preservatives such as Solbrol® (Bayer Chemicals AG); silicones; chlorophyll compounds, anti-leukoplakia agents such as beta-carotene; antioxidants such as Vitamin E; and combinations thereof. In some embodiments, the films comprise such active materials at a concentration of about 0.01 to about 30% by weight of film, from about 2% to about 25% by weight of the film, or from about 10% to about 20% by weight of film.

In certain embodiments, the film and/or oral care composition includes a preservative. A preservative can be added in amounts from about 0.001 wt % to about 5 wt %, preferably from about 0.01 wt % to about 1 wt % of the film. Non-limiting examples of preservatives include sodium benzoate and potassium sorbate.

In certain embodiments, the entrainment of the zinc compound in the film matrix suspended in the dentifrice or other composition isolates these agents from interaction with reactive ingredients present in the composition so that the agents are maintained substantially separate from the reactive composition ingredients during manufacture and storage while subsequently being released from the film matrix when the composition is used. Isolation not only avoids adverse reactions that may occur between the zinc compound and other components that are present in the carrier material, but also avoids dissolution of the zinc compound and premature release of zinc ions, as well as reducing the astringent taste associated with the use of zinc compounds.

The compositions of the present invention comprise a carrier in which a film, or fragments, is entrained. As referred to herein, a "carrier" is any material or composition in which a film can be entrained and is suitable for administration or application to the human or animal subject to whom the composition is administered or applied. As referred to herein, "entrained" refers to the embedding or suspension of a film in a carrier. In various embodiments comprising a plurality of fragments, such fragments may be entrained by embedding, suspension, dispersion or other distribution of the fragments in the carrier. In various embodiments, the fragments are distributed substantially homogenously throughout the carrier. In other embodiments, the fragments are not distributed homogenously in the carrier. In certain embodiments, the distribution of a plurality of film fragments is substantially isotropic within the carrier. Dentifrice compositions that include a plurality of film fragments dispersed or suspended in a carrier are commercially available under the tradename Max Fresh® or Max White®, from Colgate-Palmolive Company, New York, N.Y.

The film includes a zinc compound that provides a source of zinc ions. Zinc ions have been found to help in the reduction of gingivitis, plaque, sensitivity, and improved breath benefits. Many zinc compounds, however, are sparingly soluble and hence, must be used in relatively large amounts to provide an effective amount of zinc ions. Unfortunately, many zinc compounds also have unpleasant consumer astringency, especially when used in relatively high concentration. The present invention provides a mechanism that increases the availability of soluble zinc, thus permitting the use of lower concentrations of zinc compounds to achieve the same or more beneficial effect.

The presence of zinc compound in a film allows incorporation of a relatively insoluble compound into a dentifrice. The method of action of films in dentifrice formulations typically is based on the mucoadhesiveness of the film and subsequent retention of the films in the mouth, as the insolubility of the zinc presumably would limit its usefulness during the 1-2 minutes of consumer brushing. The present inventors have found that the incorporation of a zinc compound into a film, coupled with a polysaccharide and a maleic anhydride copolymer system, dramatically improves the solubility of the zinc and enables an increase in the amount of zinc to levels that are commensurate with currently marketed zinc citrate formulations, which have been clinically proven to have anti-plaque and anti-gingivitis efficacy.

The oral compositions of the preferred embodiments include a zinc compound in a film that provides a source of zinc ions. The zinc compound can be a soluble or sparingly soluble compound of zinc with inorganic or organic counter ions. Examples include the fluoride, chloride, chlorofluoride, acetate, hexafluorozirconate, sulfate, tartrate, gluconate, citrate, lactate, malate, glycinate, pyrophosphate, metaphosphate, oxalate, phosphate, carbonate salts, and oxides of zinc. Preferably, the zinc compound is zinc oxide, and is used as a replacement for conventional anti-bacterial agents such as triclosan.

The amount of zinc compound included in the film can vary from about 20% to about 60% by weight, preferably from about 25% to about 55%, more preferably from about 30% to about 55%, and most preferably about 50% by weight. The amount of film included in the oral composition also can vary anywhere from about 0.1% to about 5.0%, more preferably from about 0.25% to about 3.0%, and most preferably from about 0.5% to about 2.0% by weight film. The amount of zinc compound employed in the overall oral composition therefore can vary from about 0.5 to about 2.5 wt %, based on the total weight of the composition, typically from about 1 to about 2 wt %, based on the total weight of the oral care composition.

Zinc ions are derived from the zinc compound present in the film in the dentifrice composition in an effective amount. An effective amount of zinc ions is defined as from at least 1000 ppm zinc ion, preferably 2,000 ppm to 15,000 ppm. More preferably, zinc ions are present in an amount from 3,000 ppm to 13,000 ppm and even more preferably from 4,000 ppm to 10,000 ppm. This is the total amount of zinc ions that is present in the compositions for delivery to the tooth surface.

Examples of suitable zinc compounds that serve as zinc ion sources are zinc oxide, zinc sulfate, zinc chloride, zinc citrate, zinc lactate, zinc gluconate, zinc malate, zinc tartrate, zinc carbonate, zinc phosphate, and other salts listed in U.S. Pat. No. 4,022,880.

The zinc compound can be incorporated into the film using techniques known in the art. For example, the zinc compound can be formed in a slurry with the polymer or polymer mixture forming the film, together with additives such as propylene glycol, Polysorbate 80 (Tween 80), water, flavorants, colorants, and the like, and the slurry dried to form a film. Other methods of making the film are known and described in, for example, U.S. Pat. No. 6,669,929, and U.S. Patent Application Publication No. 2003/0053962, the disclosures of which are incorporated by reference herein in their entirety. It is preferred that the zinc compound is zinc oxide, and is present in the dried film in an amount of about 50% by weight, based on the total weight of the film.

The compositions of the embodiments may be described as comprising two phases, wherein one phase comprises a carrier and a second phase comprises the aforementioned film or fragment. The term "phase" as used herein denotes a physical phase as understood in the physical and material sciences, i.e., a portion of a material whose properties and composition are uniform. However, a phase as used herein can be discontinuous, i.e., a phase can comprise a plurality of separate components. For example, a plurality of polymer film fragments of identical composition is considered to comprise a single phase. In some embodiments, a film fragment can be entirely embedded within the material comprising the first phase, or totally or partially exposed on the surface of the first phase. For example, if the composition is a dentifrice comprising both a gel and film fragments, a film fragment can be totally surrounded by the gel, or partially or totally exposed on the surface of the gel. In certain embodiments, compositions comprise more than two phases. Such multi-phase compositions include those having two carriers, each of which contributes a phase to the composition, in addition to film fragments as described herein. Other multi-phase compositions include those having a single carrier and two or more pluralities of fragments, wherein the pluralities of fragments have differing compositions.

In various embodiments, the carrier is a liquid, semi-solid or solid. A "liquid" can be a liquid of low or high viscosity. A liquid can be a liquid such that flow is imperceptible under ambient conditions. For example, a soap, such as an ordinary bar of hand soap, can be considered a liquid herein. A liquid can be a thixotropic liquid. A "semi-solid" as used herein can be a gel, a colloid, or a gum. As used herein, semi-solids and liquids are fluids distinguished on the basis of viscosity: a semi-solid is a high viscosity fluid, while a liquid has lower viscosity. There is no definitive dividing line between these two types of fluids. A semi-solid can, in certain embodiments, have a viscosity as high as thousands of mPa·s. Carriers among those useful herein include liquids, pastes, ointments, and gels, and can be transparent, translucent or opaque.

In certain embodiments, the compositions of the present invention are oral care compositions, suitable for administration to the oral cavity. Such compositions include dentifrices, mouthwashes, dental gels, lozenges, beads, gums, oral strips, mints, liquid toothpastes, sprays, paint-on gels, lip balms, whitening strips, breath strips, oral chews, and combinations thereof. An oral care composition disclosed herein can be used, for example, for cavity prevention, whitening, plaque prevention or reduction, gingivitis prevention or reduction, tartar control, sensitivity prevention or reduction, or breath malodor prevention or reduction, and stain prevention.

The specific composition of the carrier preferably depends on the intended use of the composition. In various embodiments, the carrier is aqueous, comprising from about 5% to about 95% water or from about 10% to about 70% water. In other embodiments, the carrier is substantially non-aqueous. In a dentifrice carrier, water content can be from about 5% to about 70%, from about 10% to about 50%, or from about 20% to about 40%. When the presence of water will cause the film to disintegrate, it is particularly preferred that the dried film contain no free water, in which the amount of water is substantially 0%, or negligible.

The carrier may comprise any of a variety of materials, including emulsifiers, thickeners, fillers, and preservatives. In some embodiments, the carrier may include a functional or active material, such as those described above. In some embodiments, the carrier comprises the same functional material as the film.

In one embodiment, the carrier is suitable for use as a dentifrice. In some embodiments, the carrier comprises a humectant, such as glycerine, sorbitol or an alkylene glycol such as polyethylene glycol or propylene glycol. In some configurations, the carrier comprises a humectant at a level of from about 10% to about 80% by weight, or about 20% to about 60% by weight of the composition. Carrier compositions among those useful herein are disclosed in U.S. Pat. No. 5,695,746, Garlick, Jr., et al, and U.S. Pat. No. 4,839,157, Mei-King Ng et al.

In various dentifrice embodiments, the carrier comprises thickeners, gelling agents or combinations thereof. Thickeners or gelling agents useful herein include inorganic, natural or synthetic thickeners or gelling agents. In some configurations, the carrier comprises the thickener and gelling agent at total levels of from about 0.10% to about 15% by weight, or from about 0.4% to about 10% by weight of the composition. Examples of thickeners and gelling agents useful herein include inorganic thickening silicas such as: an amorphous silica, for example Zeodent® 165 (Huber Corporation); Irish moss; iota-carrageenan; gum tragacanth; or polyvinylpyrrolidone. In certain embodiments, the carrier comprises a polishing agent, such as a silica, a calcined alumina, sodium bicarbonate, calcium carbonate, dicalcium phosphate or calcium pyrophosphate. In various embodiments, the carrier can be a visually clear composition.

In various dentifrice embodiments, comprising a visually clear carrier, the composition comprises at least one polishing agent. Polishing agents among those useful herein include collodial silica, such as, for example, Zeodent® 115 (Huber Corporation), and alkali metal aluminosilicate complexes (i.e., a silica comprising alumina). In some configurations, a polishing agent can have a refractive index close to that of a gelling agent combined with water and/or humectant. In various embodiments, the carrier comprises the polishing agent at a level of from about 5% to about 70% by weight of the composition.

In certain dentifrices, the carrier comprises a surfactant or mixture of surfactants. Surfactants among those useful herein include water-soluble salts of at least one higher fatty acid monoglyceride monosulfate, such as the sodium salt of the monsulfated monoglyceride of hydrogenated coconut oil fatty acids; cocamidopropyl betaine; a higher alkyl sulfate such as sodium lauryl sulfate; an alkyl aryl sulfonate such as sodium dodecyl benzene sulfonate; a higher alkyl sulfoacetate; sodium lauryl sulfoacetate; a higher fatty acid ester of 1,2-dihydroxy propane sulfonate; and a substantially saturated higher aliphatic acyl amides of a lower aliphatic amino carboxylic acid, such as those having 12 to 16 carbons in the fatty acid, alkyl or acyl radicals; and mixtures thereof. Amides can be, for example, N-lauroyl sarcosine, and the sodium, potassium, and ethanolamine salts of N-lauroyl, N-myristoyl, or N-palmitoyl sarcosine. In various embodiments the carrier comprises the surfactant at a level of from about 0.3% to about 5% by weight of composition, or about 0.5% to about 3% by weight of composition.

The present invention also provides methods for making a dentifrice carrier. In one embodiment, water and at least one humectant are dispersed in a conventional mixer until a first homogeneous gel phase is formed. A polishing agent is added into the first homogeneous gel phase. The first homogeneous gel phase and the polishing agent are mixed until a second homogeneous gel phase is formed. A thickener, flavorant and surfactants are added to the second homogeneous gel phase. These ingredients are mixed at high speed under vacuum of about 20 to 100 mmHg.

The compositions of the present invention are preferably stable under normal conditions of storage. As referred to herein, "stable" refers to the lack of significant adverse effect on one, and preferably all, compositional attributes such as appearance, flavor, rheology, and chemical composition of the composition. Preferably, stability in the present compositions includes the compositional and physical stability of film (including fragments, if any) in the composition. In various embodiments a composition comprising a film is stable upon storage at ambient temperature for at least about two years. It is understood, however, that in some embodiments, an otherwise stable film can disintegrate during use (as discussed above), for example, during toothbrushing using a dentifrice composition.

In certain embodiments, a composition can comprise, in addition to film fragments as described herein, two or more carriers, each of which contributes a phase to the composition. Such a composition can be stable to color bleeding. For example, a composition can include film fragments and a striped dentifrice such as that disclosed in U.S. Pat. No. 6,315,986, Wong et al. In certain embodiments, the film fragments can be of different color(s) than the stripe(s) for enhanced aesthetic appeal.

The present inventors have found that when using zinc compounds contained in a film, increasing the amount of film in the overall composition (e.g., from about 0.5% to about 2.0% by weight), does not increase the amount of soluble zinc. For example a film containing about 50% by weight zinc present in an amount of about 0.5% by weight based on the total weight of the composition, provides about 0.07% soluble zinc. In a similar manner, a film containing about 50% by weight zinc present in an amount of about 2.0% by weight based on the total weight of the composition, also provides about 0.07% soluble zinc. The present inventors found, quite unexpectedly, that use of a combination of a polysaccharide and a maleic anhydride copolymer together with the zinc-containing films provides a nearly 6-fold increase in the amount of soluble zinc.

Compositions that include zinc compounds, (not included within a film), triclosan, and a polysaccharide are described in, for example, PCT application number PCT/US09/39268, filed Apr. 2, 2009, entitled "Dentifrice Composition," the disclosure of which is incorporated by reference herein in its entirety.

The maleic anhydride copolymer preferably is a Gantrez polymer. These polymers have been described previously as antibacterial enhancing agents. One particularly preferred class of antibacterial enhancing agents includes 1:4 to 4:1 copolymers of maleic anhydride or acid with another polymerizable ethylenically unsaturated monomer. For example, one typical maleic anhydride copolymer includes a methyl vinyl ether/maleic anhydride copolymer having a molecular weight ("M.W.") ranging from 30,000 to abut 5,000,000 g/mole, or from 30,000 to 500,000 g/mole. These copolymers are commercially available, for example, under the trademark Gantrez, including Gantrez AN 139 (M.W. 500,000 g/mole), AN 119 (M.W. 250,000 g/mole); and Gantrez S-97 Pharmaceutical Grade (M.W. 700,000 g/mole), of ISP Corporation. In a preferred embodiment, the maleic anhydride copolymer typically comprises a methyl vinyl ether/ maleic anhydride copolymer having a molecular weight ranging from 30,000 to abut 1,000,000 g/mole.

When a maleic anhydride copolymer, such as the Gantrez polymer is used, zinc cations tend to react with certain thickening agents such as polysaccharides that may be present in the dentifrice formulation, in particular such thickening agents that are present as hydrocolloids and have a high concentration of groups, such as carboxylate groups, which are available to react by cross-linking with zinc cations. Such reactions tend to form an ionic bridge between the maleic anhydride copolymer and, for example, any cellulosic polymer present in the dentifrice composition as thickening agent. An unacceptably high viscosity in the bulk formula results from this interaction.

The present inventors have found, however, that the use of a thickening agent that has a low concentration of reactive groups, for example carboxylate groups, such as xanthan gum, either as the sole thickening agent or as one of a plurality of thickening agents, for the maleic anhydride copolymer system provides fewer sites for chemical interaction between the zinc ions and the maleic anhydride copolymer. This in turn allows for the incorporation of higher levels of the zinc salt, e.g. zinc oxide or zinc citrate, than would be possible using other thickening systems, for example based on carboxymethyl cellulose (CMC) or CMC/ Carrageenan formulas, without unacceptable increases in viscosity.

In accordance with the preferred embodiments of the present invention, a dentifrice containing a film that entrains a zinc compound can be formulated to provide two actives having different and complementary methods of action, and this can be achieved by use of a dentifrice gum system that includes, either wholly, or partly, xanthan gum. The dentifrice can employ high levels of the zinc active, for example by using zinc oxide at a relatively high level of from 1 to 2% by weight, based on the weight of the composition, without detrimental effects to the product aesthetics as a result of an unacceptable increase in viscosity. A particularly preferred amount of zinc citrate for use against plaque and gingivitis is 2% by weight, based on the weight of the composition.

Without wishing to be bound by any theory of operation, the present inventors believe that any compatibility between zinc cations and a maleic anhydride copolymer system is significantly reduced when certain hydrocolloids are also present in the composition. This is due to ionic bridging occurring between the maleic anhydride copolymer and the hydrocolloid, which is facilitated by the divalent cationic nature of the zinc cations. Carboxymethyl cellulose (CMC), which is such a hydrocolloid employed as a thickener, is especially prone to this binding due to the amount and nature of the substituted groups along the backbone. In order to use zinc in the presence of triclosan and maleic anhydride copolymer, such as the Gantrez product, this reaction preferably is removed or limited.

Both CMC and xanthan gum contain carboxylate groups along their backbones. While both materials are charged polysaccharides, the density of charged carboxylate groups along the backbone is quite different and much higher for the CMC than for the xanthan gum. For example, one known commercially available CMC, CMC 2000S (available from CPKelco) has a degree of substitution of ~0.9 carboxylate groups per sugar residue. Xanthan gum, in comparison, has a degree of substitution of <0.4 carboxylate groups per sugar residue. The number of carboxylate groups associated with the chain is important to the theological properties of a mixture that contains divalent ions such as $Zn^{2+}$ due to the fact that these ions complex with the carboxylate groups to form ionic crosslinks or bridges, with the zinc ions crosslinked to two opposing carboxylate groups.

These linkages can be formed from not only carboxylate groups found on CMC, but also sulfate groups found in other thickening agents such as i-Carrageenan. Such linkages can lead to interchain association of chains and the formation of large networks that can act to dramatically increase viscosity or solubility of the polymer species.

In part, the present inventors have found that a substitution of xanthan for CMC in a dentifrice can reduce the number of ionic linkages available for network formation, in turn leading to a decrease in formula viscosity, exhibited as composition thickness, while maintaining similar rheological character of the dentifrice incorporating the CMC gum system. Alternatively, in another embodiment, the use of hydroxyethyl cellulose (HEC), an uncharged water soluble cellulose derivative can remove all potential for ionic bridging and can produce dentifrice formulations of comparable thickness regardless of the presence of $Zn^{2+}$ cations.

In certain embodiments, the polysaccharide thickening agent has at most 0.5 charged groups per sugar residue unit along the polysaccharide backbone. For further information, see PCT Application No. PCT/US2009/039268, filed on 2 Apr. 2009, which is incorporated herein by reference.

The polysaccharide useful in the embodiments described herein therefore preferably comprises at least one of xanthan gum and hydroxyethyl cellulose. The polysaccharide thickening agent typically consists of at least one of xanthan gum and hydroxyethyl cellulose. Preferably, the polysaccharide thickening agent consists of xanthan gum which is present in an amount of from 0.1 to 1.5 wt % based on the weight of the composition, preferably from 0.5 to 1 wt % of the composition.

The dentifrice composition conventionally includes thickening agents that provide the dentifrice with the required rheological properties, so that the dentifrice can be stored in a dispensing container over a period of time and thereafter reliably dispensed therefrom by the user. The dentifrice preferably should have the correct viscosity not only to be dispensed but also to exhibit an acceptable consistency within the mouth during tooth brushing. Typical thickening agents include modified celluloses, such as carboxymethyl cellulose (CMC), and other polysaccharide or gum components.

The polysaccharide thickening agent may comprise at least one of xanthan gum and hydroxyethyl cellulose. The polysaccharide thickening agent typically consists of at least one of xanthan gum and hydroxyethyl cellulose. Preferably, the polysaccharide thickening agent consists of xanthan gum which is present in an amount of from 0.1 to 1.5 wt % based on the weight of the composition, preferably from 0.5 to 1 wt % of the composition. However, minor amounts of additional thickeners may be present, for example carrageenan, gum tragacanth, starch, polyvinylpyrollidione, hydroxyethypropyl cellulose, hydroxybutyl methyl cellulose, hydroxypropyl methylcellulose, hydroxyethyl cellulose, sodium carboxymethyl cellulose (sodium CMC) and colloidal silica. In one embodiment, the thickener concentration ranges of 0.1 wt. % to 5 wt. % based on the weight of the composition. In another embodiment, the thickener concentration ranges of 0.5 wt. % to 2 wt. % based on the weight of the composition.

In certain embodiments, an amount of polysaccharide thickening agent/maleic anhydride copolymer in the oral care composition is 0.5% to 5% by weight.

In some embodiments, a pyrophosphate material also is included in the carrier. The pyrophosphate material may be a sodium pyrophosphate or a tetrasodium pyrophosphate material (TSPP).

The present inventors have found that the combination of the polysaccharide thickening agent and the maleic anhydride copolymer system unexpectedly and dramatically increases the solubility of the zinc present in the film. This permits the use of a zinc source in an amount that does not create problems with consumer astringency, while at the same provides increased therapeutic and fresh breath benefits. The relatively inert polysaccharide thickening agent and maleic anhydride copolymer system also is not believed to disrupt the stability of the zinc-containing film in the product during normal product shelf-life/use.

The embodiments also provide processes for making compositions comprising a film entrained in a carrier. In various embodiments, a plurality of fragments are combined with a carrier. In some configurations, a carrier and a plurality of film fragments can be mixed. In some configurations, the mixing can comprise slow stirring. In one preferred embodiment, the process for making the composition comprising a carrier having distributed therein a plurality of lamellar fragments includes:

(a) providing the carrier including a polysaccharide thickening agent and a maleic anhydride copolymer;
(b) adding lamellar fragments of a film containing a zinc compound to the carrier to form a mixture; and
(c) homogenizing the mixture.

The term "homogenizing" as used herein refers to the admixture of the fragments and the carrier so as to attain a substantially homogeneous distribution of fragments in the carrier. It should be noted, however, that the resulting composition still retains two-phase composition characteristics. Homogenizing may be accomplished using any of a variety of conventional homogenizers.

In another method, the film is added to a component of the carrier (e.g., to a humectant for a dentifrice). The remainder of the carrier then may be made, and the mixture of film then added to the carrier.

Certain embodiments described herein also provide methods for administering a zinc compound to a human or animal subject. As referred to herein, "administering" refers to any method by which a composition is applied on or administered to the subject. In various embodiments, the administration is topical, wherein the composition is applied to an external surface of the subject, such as to a surface of the oral cavity (e.g., teeth, gingival, and tongue. The specific route and method of administration will depend, of course, on the intended use of the composition.

In various embodiments, the present invention provides methods for administering a functional material to a human or animal subject in need thereof, comprising topically applying to said subject a composition comprising a film entrained in a carrier, wherein said film comprises the functional material. In one embodiment, the method additionally comprises disrupting the film after topically applying the film. Such disruption may be accomplished by any of a variety of methods, including chemical and/or mechanical means. Chemical means include degradation of the film by contact with water or a material present at the site of administration (e.g., saliva in an oral care application). Physical means include agitation, grinding, and shear forces produced by application of physical energy to the composition during use (e.g., brushing in a dentifrice application).

In various embodiments, the present invention provides methods for the treatment of an oral care condition. As referred to herein, an "oral care condition" is any disorder or condition which can be prevented or treated by administration of a composition to the oral cavity, including disorders or conditions of the teeth, oral mucosa, gingiva and tongue. Such conditions include caries, gingivitis, periodontitis, and cosmetic conditions such as yellowing and malodour.

The embodiments described herein can be further understood by reference to the following non-limiting examples.

Example 1

This example illustrates, in table 1, how varying the amount of film containing the same amount of zinc compound, (50% by weight), does not increase the amount of soluble zinc available.

Films were made in accordance with the procedures outlined in U.S. Pat. No. 6,669,929, and U.S. Patent Application Publication No. 2003/0053962, in which the films contained, on a dry weight basis, 50% by weight of zinc oxide. Films containing 50% by weight zinc oxide can be prepared as described in U.S. Provisional Patent Application No. 61/181,124, filed on 26 May 2009, entitled: "Higher Loading Zinc-Containing Films," the disclosure of which is incorporated by reference herein in its entirety. The formula and procedure for making 50% by weight zinc oxide from application Ser. No. 61/181,124 is reproduced below.

Formula

| Material | Supplier | Slurry Weight % | Dry Weight |
|---|---|---|---|
| Hydroxypropyl methylcellulose HPMC E5 | Dow Chemical | 6.2 | 16.8 |
| Hydroxypropyl methylcellulose HPMC E50 | Dow Chemical | 5.6 | 15.2 |
| Zinc Oxide (AZO 66USP) | US Zinc | 18.7 | 50.2 |
| Propylene Glycol | Univar | 5 | 13.7 |
| Polysorbate 80 | Croda | 0.3 | 0.8 |
| Menthol | | 1.2 | 3.3 |
| Water (DI) | — | 63 | — |
| Total (%) | — | 100 | 100 |

The slurry is prepared by heating deionized water to about 80° C. About half of the formula amount of water is added to a beaker. Next, HPMC E5 is added and mixed with an overhead mixer until the polymer is wet. HPMC E50 is then added, and the slurry is mixed for 20 min with intermittent scraping of the beaker walls to ensure polymer incorporation. The ZnO powder is then added along with the remaining amount of water. After 15 min of mixing, the propylene glycol and the polysorbate 80 are added. The slurry is complete after an additional 20 min mixing. Air bubbles in the slurries are removed by mixing with the SpeedMixer™ DAC 150 FVZ for 5 min at 1800 rpm. The film is then cast and dried as described in U.S. Pat. No. 6,669,929.

The films then were incorporated into a commercially available dentifrice known as Max Fresh®, commercially available from Colgate-Palmolive Company, New York, N.Y. The Product listed in the table below is the Max Fresh product with varying amounts of film (each film containing 50% by weight of zinc oxide), or Max Fresh containing 1.0% by weight zinc oxide powder

TABLE 1

| Product | Soluble Zinc | Total Zinc |
|---|---|---|
| 0.5% film (50% Zn) | 0.07% | 0.16% |
| 1.0% film (50% Zn) | 0.06% | 0.41% |
| 2.0% film (50% Zn) | 0.07% | 0.92% |
| 1.0% zinc oxide powder | 0.07% | 0.71% |

The table shows that soluble zinc levels do not exhibit a dose response (i.e., greater levels of film does not increase soluble zinc levels in the dentifrice). In addition, the table shows that the zinc oxide-containing films do not provide a different level of soluble zinc than a commensurate amount of zinc oxide powder added directly to the dentifrice formulation, without being contained in a film.

Example 2

This example illustrates how the addition of xanthan/Gantrez polymer system (with and without tetrasodium pyrophosphate (TSPP)), dramatically increases the soluble zinc levels over those shown in Table 1 above. The amount of xanthan/Gantrez polymer used in the carrier portion of the MaxFresh dentifrice base was about 1.95% by weight.

TABLE 2

| Product | Soluble Zinc | Total Zinc |
|---|---|---|
| 2.0% film (50% zinc oxide) without TSPP | 0.30% | 1.00% |
| 2.0% film (50% zinc oxide) with TSPP | 0.23% | 0.90% |

As shown in Table 2, the use of a xanthan/Gantrez polymer system increases the amount of soluble zinc from about 0.07% to about 0.30% or 0.23%, given about the same amount of total zinc employed. This amounts to a nearly 4-fold increase in the amount of soluble zinc available.

Example 3

This example illustrates, in Table 3, various combinations of zinc oxide-containing films, each containing 50% by weight zinc oxide, together with various concentrations of xanthan/Gantrez polymer system (referred to as "Gantrez" in Table 3), and use of TSPP.

TABLE 3

| Film Conc. | Gantrez Conc. | TSPP | Soluble Zinc |
|---|---|---|---|
| 2 | 1.95 | Yes | 0.30% |
| 2 | 1.95 | No | 0.23% |
| 2 | 1.5 | Yes | 0.24% |
| 2 | 1 | Yes | 0.18% |
| 2 | 1.5 | No | 0.17% |
| 2 | 1 | No | 0.15% |
| 1 | 1.95 | Yes | 0.22% |
| 0.5 | 1.95 | Yes | 0.14% |
| 1 | 1.95 | No | 0.16% |
| 0.5 | 1.95 | No | 0.12% |
| 2 | 0 | Yes | 0.06% |

A response surface analysis indicates that film concentration and Gantrez concentration are both factors in determining the soluble zinc values, with little or no significant interaction terms. Table 3 shows that, with respect to soluble zinc, 1% or even 0.5% of film can provide greater availability of zinc with the use of the xanthan/Gantrez polymer system, than a 2% film with no polymer system (bottom comparative value in Table 3). Indeed, the xanthan/Grantrez polymer system provides nearly a 6-fold increase in available zinc, from 0.05% soluble zinc when no polymer system was utilized, to 0.30% soluble zinc when the polymer system was utilized.

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

What is claimed is:

1. An oral care composition comprising
   a film entrained in a carrier, a zinc-containing compound contained in the film,
   a polysaccharide thickening agent, and
   a maleic anhydride copolymer,
   wherein the polysaccharide thickening agent has less than 0.4 charged groups per sugar residue unit along the polysaccharide backbone; and
   wherein the film is present in an amount of 0.1% to 5% by weight of the composition and the film contains about 50% by weight of the zinc containing compound; and
   wherein the zinc-containing compound comprises zinc oxide;
   wherein the film comprises a combination of two different molecular weights of hydroxypropyl methylcellulose; and
   wherein the polysaccharide thickening agent comprises xanthan gum.

2. The oral care composition of claim 1, wherein the film further comprises propylene glycol and polysorbate 80.

3. The oral care composition of claim 1, wherein the maleic anhydride copolymer comprises a methyl vinyl ether/maleic anhydride copolymer having a molecular weight of 30,000 to 5,000,000 g/mole.

4. The oral care composition of claim 1, wherein the amount of polysaccharide thickening agent/maleic anhydride copolymer in the oral care composition is 0.5% to 5% by weight.

5. The oral care composition of claim 1, wherein
   a) the film further comprises propylene glycol and polysorbate 80;
   b) the maleic anhydride copolymer comprises a methyl vinyl ether/maleic anhydride copolymer having a molecular weight of 30,000 to 5,000,000 g/mole; and
   c) the amount of polysaccharide thickening agent comprising xanthan gum/maleic anhydride copolymer in the oral care composition is 0.5% to 5% by weight.

6. The oral care composition of claim 1, wherein the composition further comprises a pyrophosphate material.

7. The oral care composition of claim 6, wherein the pyrophosphate material is a sodium pyrophosphate or a tetrasodium pyrophosphate material (TSPP).

8. A method of making the oral care composition of claim 1 comprising:
   (a) providing the carrier including the polysaccharide thickening agent comprising xanthan gum and the maleic anhydride copolymer;
   (b) adding lamellar fragments of the film containing the zinc-containing compound comprising zinc oxide to the carrier to form a mixture; and
   (c) homogenizing the mixture.

9. A method for administering a zinc compound to a human or animal subject in need thereof comprising topically applying to the subject the oral care composition of claim 1.

10. The method of claim 9 further comprising disrupting the film after the topical application.

* * * * *